(12) United States Patent
Greci et al.

(10) Patent No.: US 11,287,357 B2
(45) Date of Patent: Mar. 29, 2022

(54) VORTEX FLUID SENSING TO DETERMINE FLUID PROPERTIES

(71) Applicant: Halliburton Energy Services, Inc., Houston, TX (US)

(72) Inventors: Stephen Michael Greci, Little Elm, TX (US); Michael Linley Fripp, Carrollton, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 321 days.

(21) Appl. No.: 16/484,576

(22) PCT Filed: Dec. 28, 2018

(86) PCT No.: PCT/US2018/068005
§ 371 (c)(1),
(2) Date: Aug. 8, 2019

(87) PCT Pub. No.: WO2020/139387
PCT Pub. Date: Jul. 2, 2020

(65) Prior Publication Data
US 2021/0333186 A1    Oct. 28, 2021

(51) Int. Cl.
| | |
|---|---|
| G01N 9/26 | (2006.01) |
| G01N 33/28 | (2006.01) |
| E21B 47/06 | (2012.01) |
| E21B 49/08 | (2006.01) |
| E21B 34/08 | (2006.01) |

(52) U.S. Cl.
CPC .............. *G01N 9/26* (2013.01); *E21B 47/06* (2013.01); *E21B 49/0875* (2020.05); *G01N 33/2847* (2013.01); *E21B 34/08* (2013.01)

(58) Field of Classification Search
CPC .................................. G01N 9/26; E21B 47/05
See application file for complete search history.

(56) References Cited

U.S. PATENT DOCUMENTS 3,474,670 A * 10/1969 Rupert ...................... F15C 1/16
    73/861.32
3,566,900 A *  3/1971 Black ...................... F15C 1/002
    137/83

(Continued)

FOREIGN PATENT DOCUMENTS

| DE | 4206845 A1 * | 9/1993 | ............... G01N 9/30 |
| WO | 2018063149 A1 | 4/2018 | |

OTHER PUBLICATIONS

PCT Application Serial No. PCT/US2018/068005, International Search Report, dated Sep. 26, 2019, 5 pages.

(Continued)

*Primary Examiner* — John Fitzgerald
(74) *Attorney, Agent, or Firm* — Delizio, Peacock

(57) ABSTRACT

Components and systems are disclosed for determining fluid component concentrations. In some embodiments, a vortex chamber is configured to rotationally direct fluid flow. A first pressure sensor is disposed on an inner radial position within the vortex chamber. A second pressure sensor is disposed on an outer radial position within the vortex chamber. A fluid property detector is configured to determine a fluid property based, at least in part, on pressure values detected by the first and second pressure sensors.

20 Claims, 5 Drawing Sheets

(56) References Cited

U.S. PATENT DOCUMENTS

| | | | | |
|---|---|---|---|---|
| 3,620,238 | A * | 11/1971 | Kawabata | F15C 1/02 137/810 |
| 3,712,321 | A * | 1/1973 | Bauer | F15C 1/16 137/812 |
| 4,433,573 | A | 2/1984 | Hulin | |
| 5,076,327 | A * | 12/1991 | Mettner | F15C 1/04 137/809 |
| 5,905,200 | A * | 5/1999 | Eldridge | G01F 1/20 73/202 |
| 8,584,762 | B2 * | 11/2013 | Fripp | E21B 34/08 166/373 |
| 8,893,804 | B2 * | 11/2014 | Fripp | E21B 34/08 166/373 |
| 8,905,144 | B2 * | 12/2014 | Dykstra | E21B 34/06 166/373 |
| 9,187,991 | B2 * | 11/2015 | Fripp | E21B 43/14 |
| 10,214,991 | B2 * | 2/2019 | van Petegem | E21B 43/12 |
| 10,597,984 | B2 * | 3/2020 | Moen | F16K 25/005 |
| 2002/0178803 | A1 | 12/2002 | Pelletier et al. | |
| 2004/0011561 | A1 * | 1/2004 | Hughes | E21B 17/1078 175/57 |
| 2010/0305881 | A1 | 12/2010 | Atkinson et al. | |
| 2011/0042091 | A1 * | 2/2011 | Dykstra | E21B 34/08 166/316 |
| 2011/0146975 | A1 * | 6/2011 | O'Malley | E21B 34/14 166/250.15 |
| 2013/0255960 | A1 * | 10/2013 | Fripp | E21B 43/32 166/373 |
| 2013/0277066 | A1 | 10/2013 | Fripp et al. | |
| 2014/0076547 | A1 | 3/2014 | Unalmis et al. | |
| 2015/0021019 | A1 * | 1/2015 | Veit | E21B 43/12 166/250.15 |
| 2016/0230540 | A1 | 8/2016 | Zhao et al. | |
| 2020/0300740 | A1 * | 9/2020 | Fripp | E21B 49/0875 |

OTHER PUBLICATIONS

PCT Application Serial No. PCT/US2018/068005, International Written Opinion, dated Sep. 26, 2019, 7 pages.

Jovanov, "Performance of Autonomous Inflow Control Systems", University of Stavanger, Faculty of Science and Technology, Master's Thesis, Jun. 13, 2016, 82 pages.

* cited by examiner

VORTEX FLUID SENSING TO DETERMINE FLUID PROPERTIES

TECHNICAL FIELD

The disclosure generally relates to the field of fluid flow control and more particularly to a fluid flow control system that uses fluid density measurements to determine relative fluid concentrations.

BACKGROUND ART

Fluid flow control is based on several factors including relative concentrations of fluids such as gaseous and liquid hydrocarbon deposits, water, etc. within a return production flow. For example, the relative concentration of hydrocarbons versus water, referred to as water cut, is a significant factor in determining flow control inputs, settings, and configurations in production wells. Technologies utilized to determine fluid component concentrations include density and viscosity evaluation techniques as well as electromagnetic radiation (e.g., infrared, RF, microwave) to identify fluid component signatures. Techniques for determining water cut based on fluid density include viscosity measurements and vibration resonance techniques for determining fluid densities. Production wells frequently utilize water cut sensors and associated flow control mechanisms at various points downhole and at surface portions of a production return line. For example, downhole production lines may include flow control devices configured to automatically alter flow rate based on fluid density and/or viscosity properties of fluids entering the devices.

BRIEF DESCRIPTION OF THE DRAWINGS

Embodiments of the disclosure may be better understood by referencing the accompanying drawings.

DESCRIPTION OF EMBODIMENTS

The description that follows includes example systems, methods, techniques, and program flows that embody embodiments of the disclosure. However, it is understood that this disclosure may be practiced without these specific details. In other instances, well-known instruction instances, protocols, structures and techniques have not been shown in detail in order not to obfuscate the description.

Overview

Embodiments disclosed herein include systems and methods for determining relative fluid concentrations based on relative fluid densities. In some embodiments, a flow control system includes one or more flow control assemblies comprising components configured to determine relative fluid concentrations by determining densities of components of a fluid flow. A flow control system may include one or more pressure detection devices deployed to detect pressure gradients at the inputs, outputs, and within vortex flow devices. Pressure detectors may be deployed at the intake and outflow of a vortex flow device to determine a differential pressure across the vortex flow device. Pressure detectors are deployed at various positions within a vortex chamber of the vortex flow device to detect pressure differentials within the vortex flow device. The detected differential pressure across an inlet nozzle is utilized to normalize fluid velocities within the vortex flow device. The normalized fluid velocities in combination with detected pressure differentials within the vortex chamber are processed to determine bulk fluid density based on a pressure gradient across the vortex chamber. Components with the flow control assemblies or external processing systems map the densities to fluid properties. Components within the flow control assemblies translate the fluid properties to fluid components that are utilized to modify flow control settings of the flow device.

Example Illustrations

Figure 1:
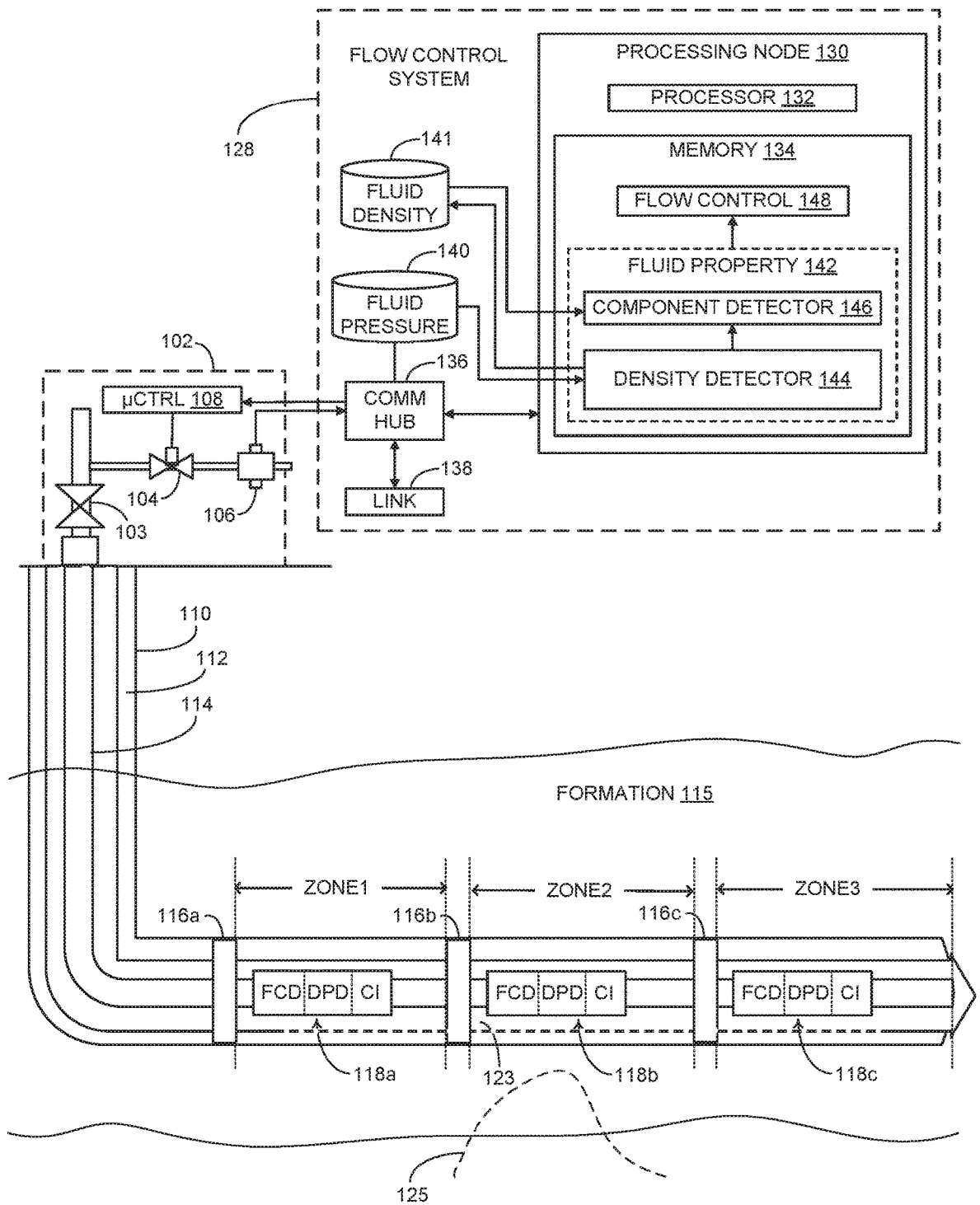
FIG. 1 is a block diagram depicting a well system that implements a vortex-type contaminant detector that can be used to control production flow in accordance with some embodiments.

FIG. 1 is a block diagram depicting a well system that implements a vortex-type contaminant detector to control production flow in accordance with some embodiments. The well system includes a well head 102 comprising components for receiving and pumping hydrocarbon fluid, such as petroleum or natural gas, from a hydrocarbon formation 115, which may be a petroleum reservoir. The components within well head 102 include pumps, valves, and other flow control components some of which are not depicted. Included among the valves is a master valve 103 that controls all surface flow from the top of a production string comprising a production conduit 114 that is sectioned into multiple flow control zones, ZONE1, ZONE2, and ZONE3. Master valve 103 controls, in part, hydrocarbon production inflow to a production valve 104, which in the depicted embodiment is electronically actuated via microcontroller 108. Microcontroller 108 and a contaminant sensor 106 that are communicatively coupled with a flow control system 128 via a communication hub 136.

The production string includes an annular casing 112, which may be cemented along the interior surface of a wellbore 110 that includes a section that is substantially vertical and a production section that is substantially horizontal. As depicted, the horizontal production sections of wellbore 110 and the production string are disposed at a depth within hydrocarbon formation 115. An inline series of flow control assemblies 118a-118c are deployed on the horizontal section of production conduit 114, each within a respective one of flow control zones, ZONE1, ZONE2, and ZONE3. The zones in the depicted embodiment comprise the portion of a production section between each of pairs of isolation packers 116a-116c that define mutually sealed sections of wellbore 110 that are interconnected by production conduit 114. Corresponding sections of casing 112 are perforated to enable fluid transmission from the surrounding formation through the wellbore 110 and into an annular region 123 within casing 112. While the depicted embodiment includes a cased production line, alternate embodiments may be implemented with production and/or injection lines that are disposed uncased within an open borehole.

Flow control assemblies 118a-118c comprise one or more types of conduit flow control devices (FCDs) such as valves, nozzles, and/or pumps, depicted in simplified block form as "FCD." Assemblies 118a-118c further include dynamic pressure detectors (DPDs), represented as block modules "DPD," as well as communication interface components represented as blocks "CI." The FCDs within assemblies 118a-118c may individually comprise a nozzle, a valve, or a combined nozzle/value device having electrically/electronically controlled fluid resistivity settings. The FCDs are configured to restrict, shut off, and/or otherwise regulate fluid flow from the annular region between production conduit 114 and wellbore 110, into production conduit 114. The FCDs may comprise self-powered pump and/or valve units that include local battery and power harvesting/generation units. Isolation packers 116a-116c typically comprise expandable elastomeric material configured to seal portions of the annulus along wellbore 110 to facilitate controlled inflow from the annulus area within casing 112 into and through sections of production conduit 114.

The DPDs within each of assemblies 118a-118c includes a combination of structural components including nozzle-fed vortex chambers in which fluid pressure sensors are disposed. Example structure of the vortex chambers, nozzles, and disposition of the pressure sensors are depicted and described with reference to FIGS. 2A, 2B, and 3. The CI components within assemblies 118a-118c may include electronic components and/or transducer components for sending and receiving message signals to and from communication hub 136 via a telemetry link 138 that provides signal transport between assemblies 118a-118c and flow control system 128. Additionally, or in the alternative, each DPD in each zone may also be configured to control the flow settings FCD in that zone without sending information to the surface for processing.

The combined structure including the FCDs together with isolation packers 116a-116c enable the flow within each of ZONE1, ZONE2, and ZONE3 to be controlled by flow control signals generated by flow control system 128 with full or partial independence. The flow control settings of the zones may be determined based on entry of fluid contaminants such as water or gas in one or more of the zones. For example, ZONE2 spans a region of wellbore 110 that is closely adjacent a water breakthrough region 125 that extends upward and into hydrocarbon formation 115 from a water layer. Breakthrough is generally a production well condition in which a liquid or gas fluid within a formation gains access into a production wellbore such as wellbore 110.

The fluid type and/or constituent components of the breakthrough fluid is a form of contaminant, the level of which is limited or otherwise controlled utilizing the fluid property detection components and systems disclosed herein. The intake pressure within the annular region within a zone, such as annular region 123 within ZONE2, is reduced by adjusting the settings of the FCD components within the zone so that fluid communication is established with production conduit 114. The pressure within the overall production conduit 114 is controlled in part by the flow setting of surface production valve 104. The flow settings of the FCDs determine corresponding pressure drops into and between the annular regions within each of the zones during production flow.

The flow control signals for controlling the settings of the FCDs are determined, at least in part, based on dynamic fluid pressure information detected by the DPDs within assemblies 118a-118c. The DPDs may include fluid flow devices configured to include vortex chambers comprising enclosed, cylindrically countered spaces in which flowing fluid is rotationally directed about a central axis line. Fluid pressure sensors are disposed on at least two different radial positions within the vortex chambers to detect dynamic fluid pressures. In some embodiments, the detected pressure values are transmitted by the communication interfaces to communication hub 136 via telemetry link 138.

Communication hub 136 forwards the detected pressure information to a fluid pressure log 140 that is configured to store the information as records associated with the respective zone in which the information was collected. For example, the fluid pressure value(s) may be recorded in association with identifies of components such as the FCDs within the zones. Fluid pressure log 140 is communicative coupled with a processing node 130 within flow control system 128 that includes components for processing the dynamic fluid pressure information to determine bulk fluid densities from which other fluid properties can be determined. Processing node 130 is configured, using a combination of hardware and software devices and programmed components, to generate fluid property information and flow control signals that account for the relative concentration of fluid component contaminants, such as water, within the bulk product fluid. The hardware within processing node 130 incudes a processor 132 configured to execute instructions corresponding to program instructions loaded into an associated memory hardware device 134.

The software stored or retrieved by or otherwise accessible for loading into memory 134 includes a fluid property detector 142 and a flow controller 148. Fluid property detector 142 is configured, using any combination of program logic, to determine one or more fluid properties based, at least in part, on pressure values detected by the downhole DPDs. Fluid property detector 142 includes a density detector 144 that is configured to compute bulk fluid density using, in part, the pressure values and normalized fluid velocity values. The bulk fluid density values may be computed using multivariate dynamic fluid pressure equations such as Bernoulli's equations based in part on pressure differences and a pressure gradient across a vortex chamber fluid flow device such as may be implemented in one of the DPDs. Density detector 144 may also or alternatively be configured to determined changes in bulk fluid density by tracking changes in the detected bulk fluid density over time.

In some embodiments, density detector 144 is configured to normalize a flow rate parameter for the inner and outer radial positions of the vortex chamber based, at least in part, on a pressure differential detected by the differential pressure detector disposed within an inlet nozzle the feeds into the vortex chamber. In some embodiments, the flow rate parameter may be a fluid speed or velocity. Density detector 144 is further configured to transmit the density values to a fluid density log 141 that is configured to record fluid density values in association with the respective zone in which the corresponding dynamic fluid pressure information was collected. For example, the bulk fluid density value(s) may be recorded in association with identifies of components such as the FCDs within the zones.

Fluid property detector 142 further includes a fluid component detector 146 comprising program instructions configured to determine the relative concentrations of fluid components based on the bulk fluid density values. Fluid component detector 146 may retrieve fluid density values from fluid density log 141 and calculate fluid component percentages based on a density value and known densities of water and oil. Fluid component detector 146 is further configured to determine changes in fluid component composition based on changes in density information from density detector 144 indicating changes in fluid density over time. The fluid component information is received and used by flow controller 148 to determine FCD adjustment signals that are transmitted via telemetry link 138 to one or more or the FCDs within assemblies 118a-118c.

Figure 2A:
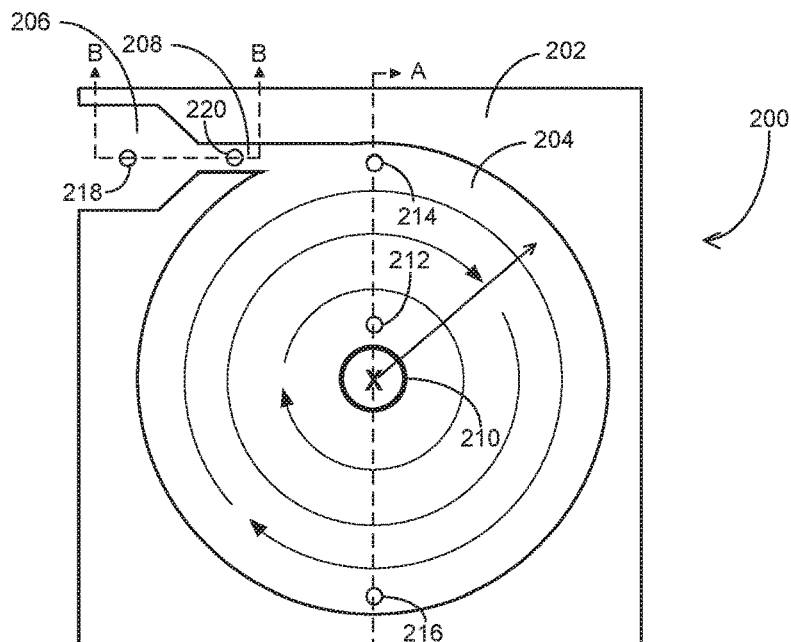
FIG. 2A illustrates an overhead cutaway view of a dynamic pressure detector in accordance with some embodiments.
Figure 2B:
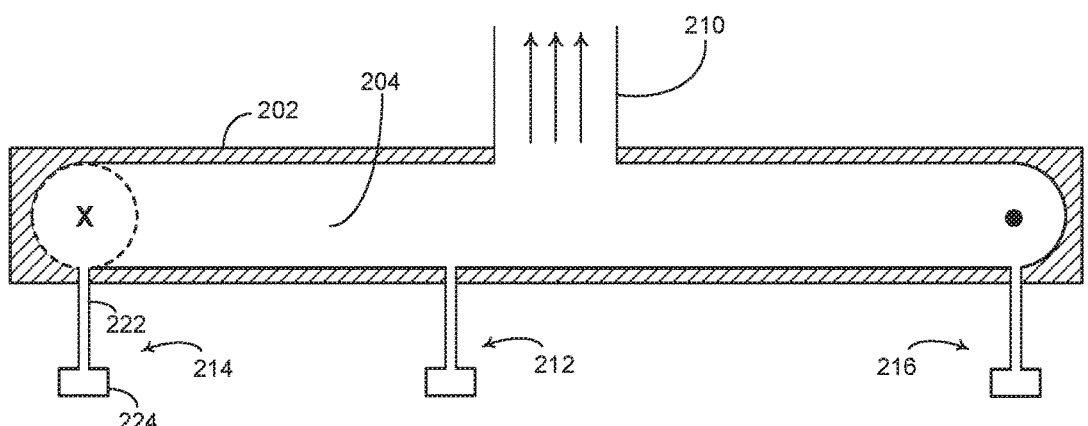
FIG. 2B depicts a cross-section view of the dynamic pressure detector illustrated in FIG. 2A.
Figure 2C:
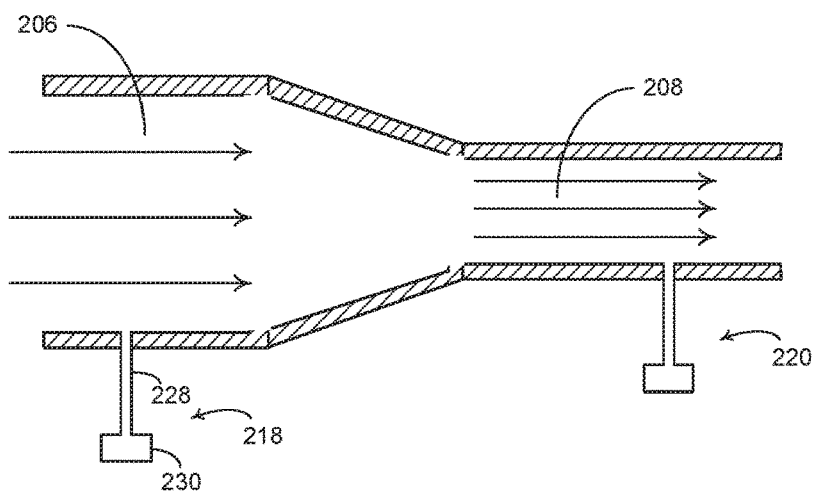
FIG. 2C illustrates a cross-section view of the nozzle differential pressure detector depicted in FIG. 2A.

FIG. 2A, FIG. 2B, and FIG. 2C illustrate an overhead cutaway view and a cross-section view of a dynamic fluid pressure detector 200 in accordance with some embodiments. The pressure detector may be implemented as one or more of the DPDs depicted and described with reference to FIG. 1. The pressure detector includes a casing 202 that encloses a cylindrically contoured inner cavity forming a vortex chamber 204. The pressure detector further includes a nozzle comprising a nozzle inlet 206 that feeds to a narrowed choke portion 208. Unlike vortex chambers described herein, which are rotational flow devices, the inlet nozzle disclosed herein include the nozzle comprising inlet 206 and choke portion 208 are non-rotational flow devices. The pressure detector further includes an outlet port 210 through which fluid flows perpendicularly to the fluid inflow through the inlet nozzle. As depicted by the curved arrows, fluid flowing into vortex chamber 204 is directed in a rotational flow about a center axis parallel to outlet port 210.

Pressure detector 200 further includes multiple pressure sensors disposed at various locations within vortex chamber 204 and the inlet nozzle. A first pressure sensor 212 is disposed on an inner radial position within vortex chamber 204 and a second pressure senor 214 is disposed on an outer radial position within vortex chamber 204. In the depicted embodiment, the pressure sensors comprise a tube portion forming a fluid path to a pressure sensing component. For example, pressure sensor 214 comprises tube portion 222 and pressure sensing component 224, which may comprise a quartz pressure sensing component. In the depicted embodiment, the pressure detector further includes a third pressure sensor 216 that is disposed on an outer radial position within vortex chamber 204 diametrically opposed to pressure sensor 214.

The pressure detector further includes a pressure sensor 218 disposed within the nozzle inlet 206 and a pressure sensor 220 disposed within the nozzle choke portion 208. The inlet nozzle pressure sensors comprise a tube portion forming a fluid path to a pressure sensing component. For example, pressure sensor 218 comprises tube portion 228 and pressure sensing component 230. Pressure sensor 218 and 220 form a pressure drop detector that in combination determine a pressure drop as fluid flows from inlet 206 and choke portion 208. The positioning of pressure sensors 212, 214, and 218 within vortex chamber 204 enables a differential pressure to be determined based on difference in pressure values detected by the sensors as fluid flows rotationally at different radial positions. The pressure values detected on the different radial positions may be utilized to determine pressure gradients between an inner and outer radial positions within vortex chamber 204. In determining pressure gradients, the pressure values determined by the nozzle pressure sensors 218 and 220 can be processed by a density detector, such as density detector 144, to normalize a fluid flow parameter such as fluid velocity within vortex chamber 204.

Figure 3:
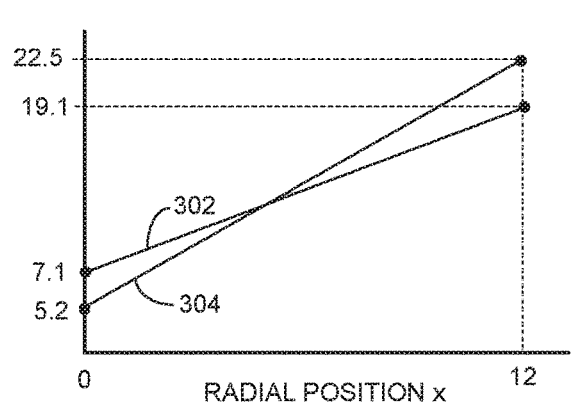
FIG. 3 illustrates radial pressure gradients that may be generated using a first dynamic fluid pressure sensor configuration.

FIG. 3 illustrates radial pressure gradients that may be generated by a density detector such as density detector 144 using a first dynamic fluid pressure sensor configuration. In the depicted embodiment, radial position 0 represents the radial position of pressure sensor 212 and radial position 12 represents the radial position of either pressure sensor 214 and/or pressure sensor 216. At radial position 0, a pressure value of 7.1 units (e.g., Pa) is detected and at radial position 12, a pressure value of 19.1 is detected at a first time. A first pressure gradient 302 is formed between the pressure values detected at the first time point. At a second time point, a pressure value of 5.2 is detected at radial position of 0 and a pressure value of 22.5 is detected at a radial position of 12. A second pressure gradient 304 is formed between the pressure values detected at the second time point.

Pressure gradients 302 and 304 each represent the magnitude and direction of pressure changes between the radial positions. The rotational fluid flow within vortex chamber 204 is a flow characterized by constant change in flow direction. In contrast, fluid flow through the inlet nozzle is a substantially non-rotational flow. A bulk fluid density of the fluid at each of the first and second time points may be determined, in part, based on pressure gradients 302 and 304, respectively. In some embodiments, the bulk fluid density values are determined based on the combination of the pressure difference determined in the non-rotational flow of the nozzle and the pressure gradient determined across the rotational flow.

Figure 4:
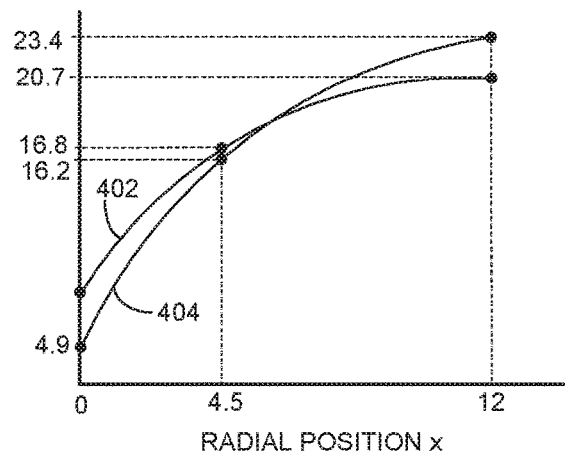
FIG. 4 depicts radial pressure gradients that may be generated using a second dynamic fluid pressure sensor configuration.

FIG. 4 depicts radial pressure gradients that may be generated using a second dynamic fluid pressure sensor configuration in which an at least three pressure sensors are disposed at different radial positions within the vortex chamber. Pressure gradients 402 and 404 each represent the magnitude and direction of pressure changes between the radial positions. A bulk fluid density of the fluid at each of the first and second time points may be determined, in part, based on pressure gradients 402 and 404, respectively. In some embodiments, the bulk fluid density values are determined based on the combination of the pressure difference determined in the non-rotational flow of the nozzle and the pressure gradient determined across the rotational flow.

Figure 5:
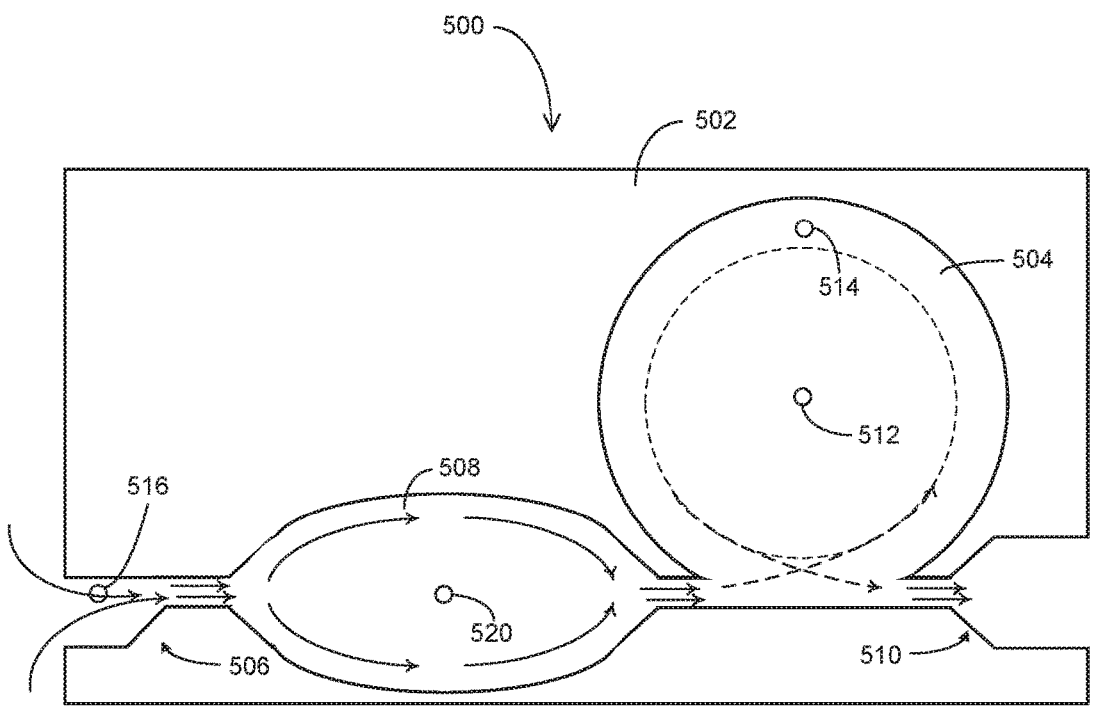
FIG. 5 illustrates an overhead cutaway view of a dynamic pressure detector in accordance with some embodiments.

FIG. 5 illustrates an overhead cutaway view of a dynamic pressure detector 500 in accordance with some embodiments. Similar to pressure detector 200, pressure detector 500 includes a cylindrically contoured vortex chamber 504 and also includes an inlet path nozzle 506 comprising in inlet port and choke portion. In contrast to pressure detector 200, the inlet/outlet flow path for pressure detector is in parallel (left to right in the figure) from the chamber inlet to an outlet 510 rather than transverse. Pressure detector 500 further includes an expansion chamber 508 disposed between the inlet nozzle and vortex chamber 504. The incoming fluid slows downs as it expands within expansion chamber. The slowing of the fluid facilitates greater accuracy of the pressure drop across nozzle 506.

Pressure detector 500 further includes multiple pressure sensors disposed at various locations within vortex chamber 504 and the inlet nozzle. A first pressure sensor 512 is disposed on an inner radial position within vortex chamber 504 and a second pressure senor 514 is disposed on an outer radial position within vortex chamber 504. Similar to the sensors shown in FIG. 2, pressure sensors 512 and 514 may comprise a tube portion forming a fluid path to a pressure sensing component. Pressure detector 500 further includes a pressure sensor 516 disposed within the inlet port of nozzle 506 and a pressure sensor 520 disposed in the expansion chamber 508. Pressure sensors 516 and 520 form a pressure drop detector that determines a pressure drop as fluid flows through nozzle 506. The positioning of pressure sensors 512 and 514 within vortex chamber 504 enables a differential pressure to be determined based on difference in pressure values detected by the sensors as fluid flows rotationally at different radial positions. The pressure values detected on the different radial positions may be utilized to determine pressure gradients between an inner and outer radial positions within vortex chamber 504. The pressure values determined by pressure sensor 516 in combination with the pressure detected by sensor 520 can be used to normalize a fluid flow parameter such as fluid velocity within vortex chamber 504.

Figure 6:
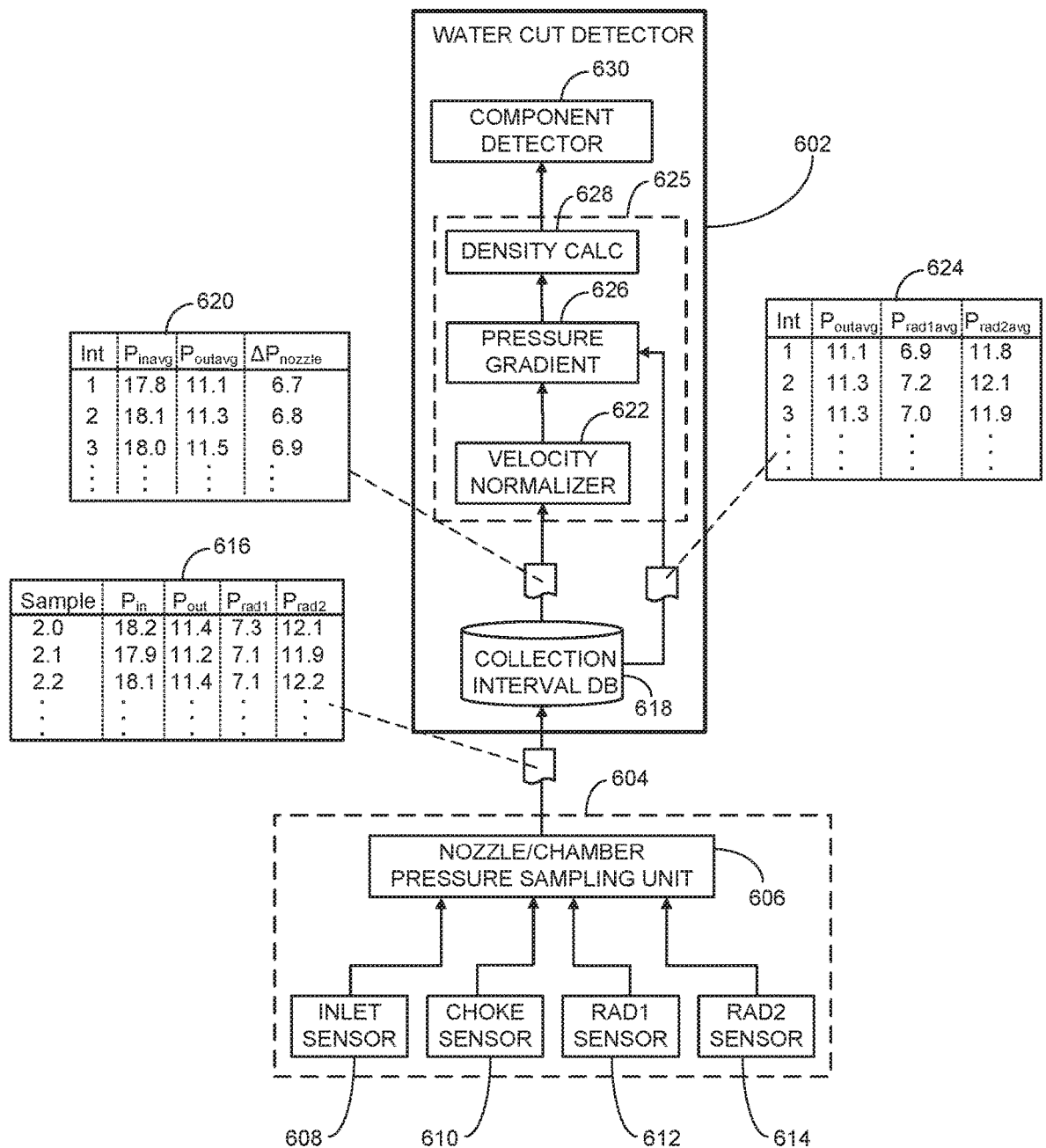
FIG. 6 illustrates a flow control system including components for determining fluid component concentrations based on turbulence pressure detection in accordance with some embodiments.

FIG. 6 illustrates a flow control system including components for determining fluid component concentrations based on turbulence pressure detection in accordance with some embodiments. The system includes a vortex pressure detector 604 comprising a pressure sampler 606 that receives detected pressure information from an inlet sensor 608, a choke sensor 610, a first vortex sensor 612, and a second vortex sensor 614. Inlet sensor 608 is disposed within an inlet port of a nozzle that constitutes or is a part of an inlet path to a vortex chamber. Choke sensor 610 is disposed on the other side of the nozzle. Vortex sensors 612 and 614 are disposed at different radial positions within a vortex chamber. For example, vortex sensor 612 may be disposed on in inner radial position and sensor 614 on in outer radial position of the vortex chamber.

Pressure sampler 606 is configured to receive and process the pressure values measured by the pressure sensors and transmit the information to a collection database 618 within a water cut detector 602. Collection database 618 is configured to generate pressure records, such as pressure records 616, that associate individual sample IDs with the respective pressure values detected by pressure sensors 608, 610, 612, and 614. In some embodiments, collection database 618 is further configured to generate measurement interval records, such as interval records 620, based on the pressure information collected across multiple samples within records 616. As shown, each of interval records 620 associates an interval that corresponds to a range of samples with values of nozzle inlet and choke pressures and average pressure drops values determined from records 616. Collection database 618 is further configured to generate vortex pressure records, such as pressure records 624, that associate sample interval IDs with respective average values for vortex chamber pressure sensors disposed at different radial positions.

The nozzle pressure drop information is processed in combination with vortex chamber pressure information by a density detector 625 to determine bulk fluid density. Density detector 625 comprises a velocity normalizer 622 that is configured to process the nozzle pressure drop information to provide flow parameter normalization data in the form of normalized fluid velocities within the vortex chamber. Velocity normalizer 622 determines the normalized fluid velocities based, at least in part, on pressure difference information detected from the pressures measured by inlet sensor 608 and choke sensor 610. A pressure gradient detector 626 is configured to process the flow normalization data in combination with the vortex chamber average pressure information in records 624 to determine pressure gradients such as those depicted in FIGS. 3 and 4.

The pressure gradient information is received and processed by a fluid density calculator 628 that is configured to determine bulk fluid density based, at least in part, on the pressure gradient information. The bulk fluid density information generated by density detector 625 is received and processed by a fluid component detector 630 that is configured to determine fluid component concentrations based on known fluid component density information and on the detected bulk fluid density. For example, if the known oil density is 700 kg/m3 and water density is 1000 $kg/m^3$, then a bulk fluid density from density detector 625 of 850 $kg/m^3$ results in a determination by component detector 630 of a water cut of 50% (i.e., the bulk fluid is 50% oil and 50% water).

Example Computer

Figure 7:
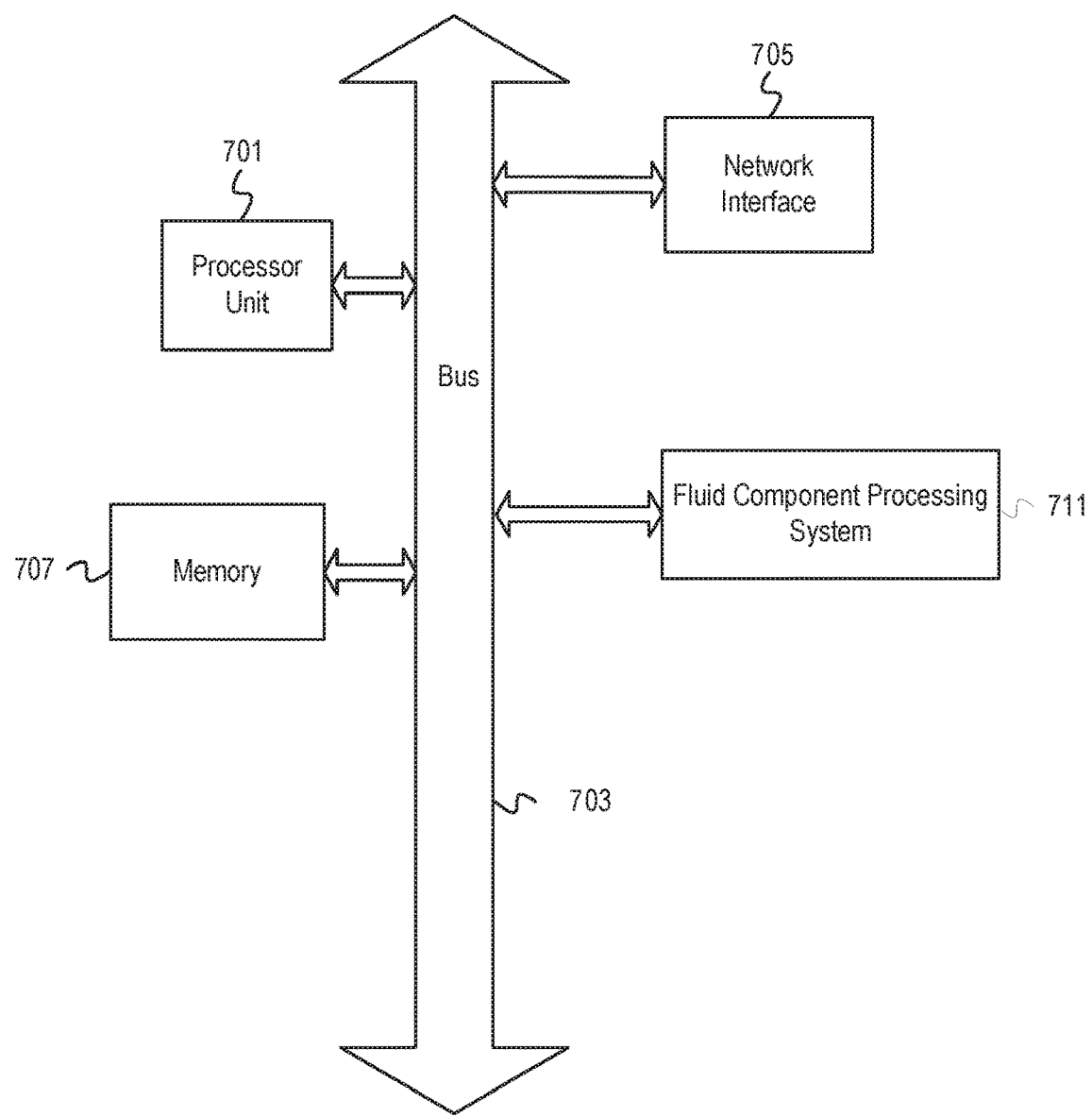
FIG. 7 depicts a computer system comprising a fluid component determination system in accordance with some embodiments.

FIG. 7 depicts an example computer, according to some embodiments. The computer system includes a processor 701 (possibly including multiple processors, multiple cores, multiple nodes, and/or implementing multi-threading, etc.). The computer system includes a memory 707. The memory 707 may be system memory or any one or more of the above already described possible realizations of machine-readable media. The computer system also includes a bus 703 and a network interface 705.

The system also includes a fluid component processing system 711, which may be hardware, software, firmware, or a combination thereof. For example, the fluid component processing system 711 may comprise instructions executable by the processor 701. Any one of the previously described functionalities may be partially (or entirely) implemented in hardware and/or on the processor 701. For example, the functionality may be implemented with an application specific integrated circuit, in logic implemented in the processor 701, in a co-processor on a peripheral device or card, etc. The fluid component processing system 711 determines fluid properties such as density based on turbulence pressure detection in the manner described above. The processor 701 and the network interface 705 are coupled to the bus 703. Although illustrated as being coupled to the bus 703, the memory 707 may be coupled to the processor 701.

Variations

While the aspects of the disclosure are described with reference to various implementations and exploitations, it will be understood that these aspects are illustrative and that the scope of the claims is not limited to them. In general, devices and techniques for determining fluid properties as described herein may be implemented with facilities consistent with any hardware system or hardware systems. Many variations, modifications, additions, and improvements are possible. Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The machine readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine readable storage medium may be any tangible medium that can contain, or store a program for use by or in connection with an instruction execution system, apparatus, or device.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

EMBODIMENTS

Embodiment 1: An apparatus comprising: a vortex chamber configured to rotationally direct fluid flow; a first pressure sensor disposed on an inner radial position within the vortex chamber; a second pressure sensor disposed on an outer radial position within the vortex chamber; and a fluid property detector configured to determine a fluid property based, at least in part, on pressure values detected by the first and second pressure sensors.

Embodiment 2: The apparatus of Embodiment 1, wherein said fluid property detector includes a fluid density detector configured to determine a pressure gradient across the vortex chamber based, at least in part, on the pressure values.

Embodiment 3: The apparatus of Embodiments 1-2, wherein the pressure gradient is determined as a slope value comprising a magnitude and direction, and wherein the fluid density detector is configured to determine a fluid density parameter based, at least in part, on the slope value.

Embodiment 4: The apparatus of Embodiments 1-3, wherein the fluid density parameter is a fluid density value, and wherein the fluid property detector is further configured to determine a component fluid composition based, at least in part, on the fluid density value.

Embodiment 5: The apparatus of Embodiments 1-4, wherein the fluid density parameter is a change in fluid density, and wherein the fluid property detector is further configured to determine a change in component fluid composition based, at least in part, on the change in fluid density.

Embodiment 6: The apparatus of Embodiments 1-5, wherein the vortex chamber comprises a substantially cylindrically countered space within a casing and configured to rotationally direct fluid about a central axis.

Embodiment 7: The apparatus of Embodiments 1-6, wherein said vortex chamber includes inlet port and an outlet port, said apparatus further comprising: a nozzle having an inlet port and a choke portion forming the inlet port of the vortex chamber; a third fluid pressure sensor disposed in the inlet port of the nozzle; and a fourth fluid pressure sensor disposed in the choke portion of the nozzle.

Embodiment 8: The apparatus of Embodiments 1-7, wherein the fluid property detector includes a flow normalizer configured to normalize a flow rate parameter for the inner and outer radial positions based, at least in part, on differences between pressure values detected by third and fourth pressure sensors.

Embodiment 9: The apparatus of Embodiments 1-8, wherein the flow rate parameter is a fluid speed.

Embodiment 10: The apparatus of Embodiments 1-9, wherein said vortex chamber includes an inlet port and an outlet port, said apparatus further comprising: a nozzle having an inlet port and a choke portion forming the inlet port of the vortex chamber; a third fluid pressure sensor disposed in the inlet port of the nozzle; an expansion chamber disposed between the nozzle and the vortex chamber; and a fourth fluid pressure sensor is disposed within the expansion chamber.

Embodiment 11: An apparatus comprising: a non-rotational flow device; a first pressure sensor disposed within the non-rotational flow device; a rotational flow device having an inlet port in fluid communication with an outlet port of the non-rotational flow device; a second pressure sensor disposed on an inner radial position within the rotational flow device; and a third pressure sensor disposed on an outer radial position within the rotational flow device.

Embodiment 12: The apparatus of Embodiment 11, wherein the non-rotational flow device comprises a nozzle that includes an inlet port and a choke portion that is narrower than the inlet port.

Embodiment 13: The apparatus of Embodiments 11-12, wherein the rotational flow device includes a cylindrically contoured vortex chamber within a casing.

Embodiment 14: The apparatus of Embodiments 11-13, further comprising a density detector configured to determine a pressure differential between fluid pressures detected by the second pressure sensor and fluid pressures detected by the third pressure sensor.

Embodiment 15: The apparatus of Embodiments 11-14, wherein the density detector is further configured to determine a pressure gradient across a radial length of the vortex chamber based at least in part on the determined pressure differential.

Embodiment 16: A system comprising: a dynamic fluid pressure detector including, an enclosed, cylindrically contoured vortex chamber; a first pressure sensor disposed on an inner radial position of the vortex chamber; and a second pressure sensor disposed on an outer radial position of the vortex chamber; and a fluid property detector including a pressure gradient detector configured to determine a pressure gradient based, at least in part, on pressures detected by the first and second pressure sensors.

Embodiment 17: The system of Embodiment 16, further comprising: a nozzle disposed at an inlet of the vortex chamber; and a differential pressure detector disposed within the nozzle.

Embodiment 18: The system of Embodiments 16-17, further comprising a velocity normalizer configured to normalize a flow rate parameter for the inner and outer radial positions of the vortex chamber based, at least in part, on a pressure differential detected by the differential pressure detector.

Embodiment 19: The system of Embodiments 16-18, further comprising a density detector configured to determine bulk fluid density based, at least in part, on the detected pressure gradient.

Embodiment 20: The system of Embodiments 16-19, wherein said vortex chamber includes an inlet port and an outlet port, said system further comprising: a nozzle having an inlet port and a choke portion forming the inlet port of the vortex chamber; a third fluid pressure sensor disposed in the inlet port of the nozzle; an expansion chamber disposed between the nozzle and the vortex chamber; and a fourth fluid pressure sensor is disposed within the expansion chamber.

What is claimed is:

1. An apparatus comprising:
   a vortex chamber configured to rotationally direct fluid flow;
   a first pressure sensor disposed on an inner radial position within the vortex chamber;
   a second pressure sensor disposed on an outer radial position within the vortex chamber; and
   a fluid property detector configured to determine a fluid property based, at least in part, on pressure values detected by the first and second pressure sensors.

2. The apparatus of claim 1, wherein said vortex chamber includes an inlet port and an outlet port, said apparatus further comprising:
   a nozzle having an inlet port and a choke portion forming the inlet port of the vortex chamber;
   a third fluid pressure sensor disposed in the inlet port of the nozzle;
   an expansion chamber disposed between the nozzle and the vortex chamber; and
   a fourth fluid pressure sensor is disposed within the expansion chamber.

3. The apparatus of claim 1, wherein the vortex chamber comprises a substantially cylindrically countered space within a casing and configured to rotationally direct fluid about a central axis.

4. The apparatus of claim 1, wherein said vortex chamber includes inlet port and an outlet port, said apparatus further comprising:
   a nozzle having an inlet port and a choke portion forming the inlet port of the vortex chamber;
   a third fluid pressure sensor disposed in the inlet port of the nozzle; and
   a fourth fluid pressure sensor disposed in the choke portion of the nozzle.

5. The apparatus of claim 4, wherein the fluid property detector includes a flow normalizer configured to normalize a flow rate parameter for the inner and outer radial positions based, at least in part, on differences between pressure values detected by third and fourth pressure sensors.

6. The apparatus of claim 5, wherein the flow rate parameter is a fluid speed.

7. The apparatus of claim 1, wherein said fluid property detector includes a fluid density detector configured to determine a pressure gradient across the vortex chamber based, at least in part, on the pressure values.

8. The apparatus of claim 7, wherein the pressure gradient is determined as a slope value comprising a magnitude and direction, and wherein the fluid density detector is configured to determine a fluid density parameter based, at least in part, on the slope value.

9. The apparatus of claim 8, wherein the fluid density parameter is a fluid density value, and wherein the fluid property detector is further configured to determine a component fluid composition based, at least in part, on the fluid density value.

10. The apparatus of claim 8, wherein the fluid density parameter is a change in fluid density, and wherein the fluid property detector is further configured to determine a change in component fluid composition based, at least in part, on the change in fluid density.

11. An apparatus comprising:
    a non-rotational flow device;
    a first pressure sensor disposed within the non-rotational flow device;
    a rotational flow device having an inlet port in fluid communication with an outlet port of the non-rotational flow device;
    a second pressure sensor disposed on an inner radial position within the rotational flow device; and
    a third pressure sensor disposed on an outer radial position within the rotational flow device.

12. The apparatus of claim 11, wherein the non-rotational flow device comprises a nozzle that includes an inlet port and a choke portion that is narrower than the inlet port.

13. The apparatus of claim 11, wherein the rotational flow device includes a cylindrically contoured vortex chamber within a casing.

14. The apparatus of claim 13, further comprising a density detector configured to determine a pressure differential between fluid pressures detected by the second pressure sensor and fluid pressures detected by the third pressure sensor.

15. The apparatus of claim 14, wherein the density detector is further configured to determine a pressure gradient across a radial length of the cylindrically contoured vortex chamber based at least in part on the determined pressure differential.

16. A system comprising:
    a dynamic fluid pressure detector including,
      an enclosed, cylindrically contoured vortex chamber;
      a first pressure sensor disposed on an inner radial position of the enclosed, cylindrically contoured vortex chamber; and
      a second pressure sensor disposed on an outer radial position of the enclosed, cylindrically contoured vortex chamber; and
    a fluid property detector including a pressure gradient detector configured to determine a pressure gradient based, at least in part, on pressures detected by the first and second pressure sensors.

17. The system of claim 16, further comprising a density detector configured to determine bulk fluid density based, at least in part, on the detected pressure gradient.

18. The system of claim 16, wherein said enclosed, cylindrically contoured vortex chamber includes an inlet port and an outlet port, said system further comprising:
    a nozzle having an inlet port and a choke portion forming the inlet port of the enclosed, cylindrically contoured vortex chamber;
    a third fluid pressure sensor disposed in the inlet port of the nozzle;
    an expansion chamber disposed between the nozzle and the enclosed, cylindrically contoured vortex chamber; and
    a fourth fluid pressure sensor is disposed within the expansion chamber.

19. The system of claim 16, further comprising:
a nozzle disposed at an inlet of the enclosed, cylindrically contoured vortex chamber; and
a differential pressure detector disposed within the nozzle.

20. The system of claim 19, further comprising a velocity normalizer configured to normalize a flow rate parameter for the inner and outer radial positions of the enclosed, cylindrically contoured vortex chamber based, at least in part, on a pressure differential detected by the differential pressure detector.

* * * * *